(12) United States Patent
Takahashi et al.

(10) Patent No.: US 7,491,822 B2
(45) Date of Patent: Feb. 17, 2009

(54) PRODUCTION METHOD OF AMINOPYRIMIDINE COMPOUND

(75) Inventors: Daisuke Takahashi, Kawasaki (JP); Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 758 days.

(21) Appl. No.: 11/081,631

(22) Filed: Mar. 17, 2005

(65) Prior Publication Data
US 2005/0215789 A1    Sep. 29, 2005

(30) Foreign Application Priority Data
Mar. 17, 2004    (JP)    .............................. 2004-077263

(51) Int. Cl.
*C07D 239/02*    (2006.01)
(52) U.S. Cl. .................................................... 544/319
(58) Field of Classification Search ................ 544/319
See application file for complete search history.

(56) References Cited

U.S. PATENT DOCUMENTS

| 4,665,175 | A | 5/1987 | Maurer |
| 6,380,206 | B1 | 4/2002 | Pamukcu et al. |
| 2004/0230053 | A1 | 11/2004 | Takahashi et al. |
| 2005/0209257 | A1 | 9/2005 | Takahashi et al. |
| 2005/0215789 | A1 | 9/2005 | Takahashi et al. |

FOREIGN PATENT DOCUMENTS

| DE | 34 23 622 | 1/1986 |
| EP | 0 647 639 | 4/1995 |
| WO | WO 02/42280 | 5/2002 |
| WO | WO 02/42290 | 5/2002 |
| WO | WO 03/106434 | 12/2003 |

OTHER PUBLICATIONS

Tikdari, et al., Reactions of Some 1,3-Diaminonucleophiles with Azlactones, J. Chem. Soc. Perk. Trans. 1, (7), pp. 1659-1659 (1988).*
N. Whittaker et al, "A New Synthesis and the Chemical Properties of 5-Aminopyrimidine", *Journal of The Chemical Society*, 1951, pp. 1565-1570.
K. Yoshida et al, "Reaction of N-Substituted Cyclic Amines with 2,4-Dichloroquinazoline, 2,4-Dichloropyrimidine, and its 5-Methyl Derivative", *J. Chem. Soc. Perkin Trans. 1*, 1992, pp. 919-922.
D. Montebugnoli et al, "Regioselective 4-amino-de-chlorination of trichloro- and dichloro-pyrimidines with N-sodium carbamates", *Tetrahedron*, vol. 58, 2002, pp. 2147-2153.
M.P. Nemeryuk et al, "Transformations of Substituted 5-Aminopyrimidines Under Conditions of The Diazotization", *Collection Czechoslovak Chem. Commun.*, vol. 51, 1986, pp. 215-233.
W.D. Dean et al, "Synthesis of 4(3H)-Quinazolinones from Derivatives of Methyl 2-Isothiocyanatobenzoate", *J. Heterocyclic Chem.*, vol. 19, 1982, pp. 1117-1124.
Accession No. 452068, "Process for the preparation of 4-chloro-2,5-dimethoxypyrimidine", *Research Disclosure*, 2001, pp. 2048-2049.
R.S. Singh et al, "Synthesis of 4-(N,N-dimethylaminomethylene)-2-alkyl-2-oxazolin-5-ones via Vilsmeier Haack reagent and their reactions with various N- and O-nucleophiles", *Indian Journal of Chemistry*, vol. 39B, 2000, pp. 688-693.
L. Kralj et al, "Aminoacids in the Synthesis of Heterocyclic Systems. The Synthesis of Methyl 2-Acetylamino-3-dimethylaminopropenoate and 2-(N-Methyl-N-trifluoroacetyl)amino-3-dimethylaminopropenoate and their Application in the Synthesis of Heterocyclic Compounds", *J. Heterocyclic Chem.*, vol. 34, 1997, pp. 247-255.
A.M. Tikdari et al, "Reactions of Some 1,3-Diaminonucleophiles with Azlactones", *J. Chem. Soc. Perkin Trans. 1*, 1988, pp. 1659-1662.
Luisa Benati et al, "Reaction of Diphenyl Disulfide with Alkynes Promoted by Di-*tert*-butyl and Dibenzoyl Peroxide: a Useful Synthetic Route to 3- (and 2,3-) Substituted Benzo[*b*]thiophenes", *J. Chem. Soc. Perkin Trans. 1*, 1992, pp. 1659-1664.
Database Crossfire Beilstein Beilstein Institut zur Foererung der Wissenschaften, Frankfurt am Main, Germany; 1988, XP002336135, Database Accession No. 162759 & Comforth, Chem., Penicillin, Princeton, 1949, p. 688 and 829.
U.S. Appl. No. 11/417,233, filed May 4, 2006, Takahashi, et al.
Luisa Benati et al, "Reaction of Diphenyl Disulfide with Alkynes Promoted by Di-tert-butyl and Dibenzoyl Peroxide: a Useful Synthetic Route to 3- (and 2,3-) Substituted Benzo[b]thiophenes", J. Chem. Soc. Perkin Trans. 1, 1992, pp. 1659-1664.

* cited by examiner

*Primary Examiner*—James O. Wilson
*Assistant Examiner*—Erich A Leeser
(74) *Attorney, Agent, or Firm*—Oblon, Spivak, McClelland, Maier & Neustadt, P.C.

(57) ABSTRACT

Aminopyrimidine compounds represented by formula (3) may be efficiently prepared by reacting an azlactone compound represented by formula (1) with an amidine compound represented by formula (2) or a salt thereof:

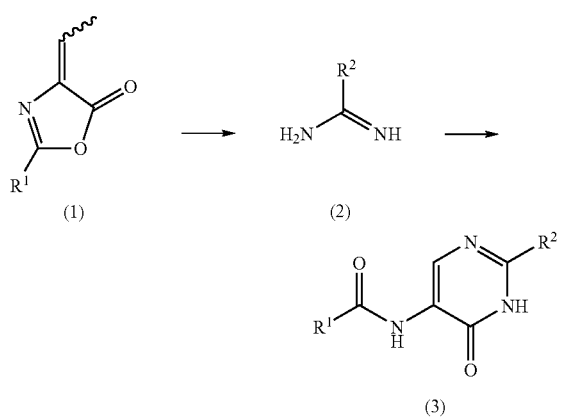

wherein $R^1$, $R^2$ and M are as defined in the specification.

12 Claims, No Drawings

PRODUCTION METHOD OF AMINOPYRIMIDINE COMPOUND

CROSS REFERENCES TO RELATED APPLICATIONS

This application claims priority to Japanese Patent Application No. 77263/2004, filed on Mar. 17, 2004, which is incorporated herein by reference in its entirety.

BACKGROUND OF THE INVENTION

1. Field of the Invention

The present invention relates to novel methods for producing aminopyrimidine compounds which are useful as intermediates for producing various compounds having pharmacological activity. The present invention also relates to certain novel aminopyrimidine compounds.

2. Discussion of the Background

Aminopyrimidine compounds represented by formula (3):

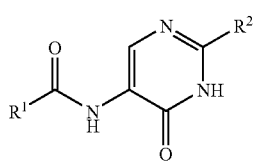

(3)

wherein R$^1$ is an alkyl group optionally having substituents or an aralkyl group optionally having substituents; and R$^2$ is an alkyl group optionally having substituents, an aryl group optionally having substituents, an aralkyl group optionally having substituents, or a group represented by the formula (a), the formula (b), or the formula (c):

(a)
(b)
(c)

wherein R$^3$ is an alkyl group optionally having substituents, an aryl group optionally having substituents, or an aralkyl group optionally having substituents; and R$^4$ is a hydrogen atom, an alkyl group optionally having substituents, an aryl group optionally having substituents, or an aralkyl group optionally having substituents, are useful as intermediates for various compounds having pharmacological activity, such as anticancer agents, NK1 antagonists, elastase inhibitors and the like (see, e.g., U.S. Pat. No. 6,380,206 and WO02/42280, which are incorporated herein by reference in their entireties).

It has long been known to introduce an amino group into the 5-position of pyrimidine by introducing a nitro group into uracil and then reducing the same (see, *J. Chem. Soc.*, pp. 1565-1570 (1951)).

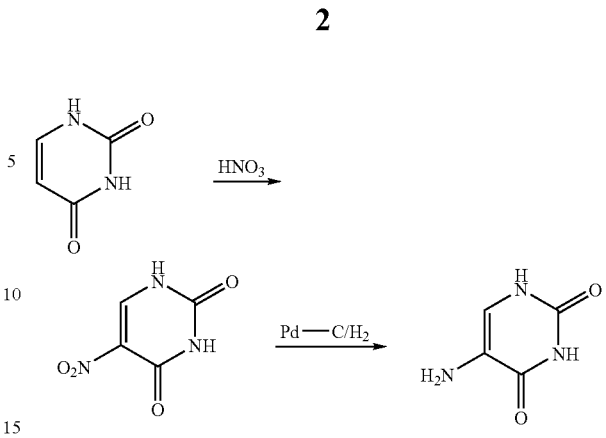

However, since nitro compounds are generally feared due to the risk of explosion, they are not necessarily suitable for an industrial production method. In addition, since uracil derivatives have a carbonyl group at both the 2-position and the 4-position, regioselective introduction of a substituent into the 2-position or the 4-position is known to be difficult (see, *J. Chem. Soc. Perk. Trans.* 1, (7), pp. 919-922 (1992), EP 647639A, and *Tetrahedron*, vol. 58 (11), pp. 2147-2153 (2002)).

As a method of producing an aminopyrimidine compound using a compound other than uracil as a starting material, for example, a method shown in the following reaction scheme has been reported (see, *J. Chem. Soc., Perk. Trans.* 1, (7), pp. 1659-1664 (1992)):

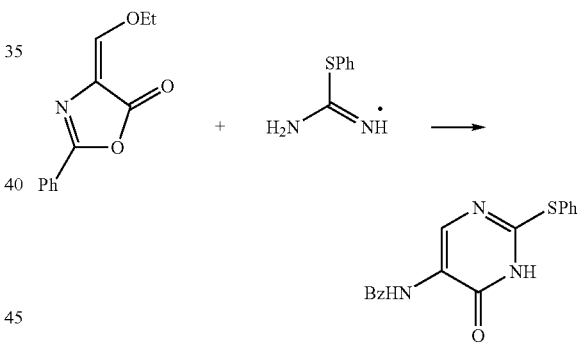

wherein Ph is a phenyl group, Et is an ethyl group, and Bz is a benzoyl group.

According to this method, however, the amino-protecting group at the 5-position is a benzoyl group, which requires severe conditions for deprotection, such as use of a strong base or a strong acid and refluxing for a long time, which in turn limits the types of groups that can be introduced into the compound. Thus, this compound is not necessarily satisfactory for use as an intermediate compound for a pharmaceutical product, and a production method capable of introducing a protecting group that can be removed under milder conditions has been desired. In contrast, when an amino group at the 5-position of an aminopyrimidine compound is protected with an aliphatic acyl group, deprotection can be performed under comparatively mild conditions. However, a compound in which 2-phenyl-4-ethoxymethylene-azlactone, which is a starting material to be used for this reaction, contains an aliphatic group at the 2-position can be obtained only in a comparatively low yield (see, WO03/106434).

A different production method comprises reacting glycine ethyl ester with ethyl formate and sodium methoxide to give an ethyl-α-formyl-formyl glycinate sodium salt, and reacting this salt with an acid addition salt of amidine in methanol to give formylaminopyrimidine (see, *Collect. Czech Chem. Comm.*, vol. 51 (1), pp. 215-233 (1986)). As regards this production method, however, there is no report on an aminopyrimidine compound, in which an amino group at the 5-position is protected with an aliphatic acyl group.

Thus, there remains a need for an improved method for producing aminopyrimidine compounds which are useful as intermediates for producing various compounds having pharmacological activity. There also remains a need for novel aminopyridine compounds which are useful as intermediates for producing various compounds having pharmacological activity.

SUMMARY OF THE INVENTION

Accordingly, it is one object of the present invention to provide novel methods for producing a compound represented by formula (3).

It is another object of the present invention to provide novel methods for producing a compound represented by formula (3) which are efficient.

It is another object of the present invention to provide novel aminopyridine compounds which are useful as intermediates for producing various compounds having pharmacological activity.

It is another object of the present invention to provide novel methods of preparing antineoplastic agents.

These and other objects, which will become apparent during the following detailed description, have been achieved by the inventors' discovery that an aminopyrimidine compound represented by formula (3) can be efficiently obtained by reacting an azlactone compound represented by formula (1), which is described below, as a starting material with an amidine compound represented by formula (2), which is described below, or a salt thereof.

Thus, the present invention provides the following:

(1) A method for producing an aminopyridine compound represented by formula (3):

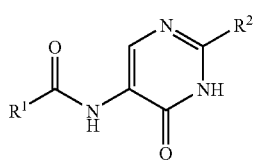  (3)

wherein $R^1$ is an alkyl group optionally having one or more substituents or an aralkyl group optionally having one or more substituents; and $R^2$ is an alkyl group optionally having one or more substituents, an aryl group optionally having one or more substituents, an aralkyl group optionally having one or more substituents, or a group represented by the formula (a), the formula (b), or the formula (c):

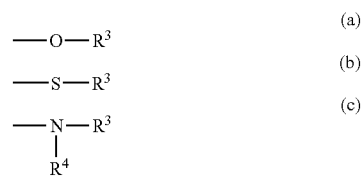

wherein $R^3$ is an alkyl group optionally having one or more substituents, an aryl group optionally having one or more substituents, or an aralkyl group optionally having one or more substituents; and $R^4$ is a hydrogen atom, an alkyl group optionally having one or more substituents, an aryl group optionally having one or more substituents, or an aralkyl group optionally having one or more substituents, wherein said method comprises reacting a azlactone compound represented by formula (1):

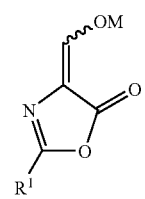  (1)

wherein M is a hydrogen atom or an alkali metal atom; a wavy line indicates a cis form, a trans form, or a mixture thereof; and $R^1$ is as defined above, with an amidine compound represented by formula (2):

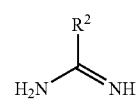  (2)

wherein $R^2$ is as defined above, or a salt thereof.

(2) The method of the above-mentioned (1), wherein $R^1$ is a linear or branched chain alkyl group having 1 to 20 carbon atoms, which optionally has one or more substituents, or an aralkyl group optionally having one or more substituents, wherein the aryl moiety in said aralkyl group is an aryl group having 6 to 12 carbon atoms and the alkyl moiety in said aralkyl group is a linear or branched chain alkyl group having 1 to 6 carbon atoms.

(3) The method of the above-mentioned (2), wherein $R^1$ is a methyl group, an ethyl group, or a benzyl group.

(4) The method of the above-mentioned (1), wherein $R^2$ is a linear or branched chain alkyl group having 1 to 20 carbon atoms, which optionally has one or more substituents, an aryl group having 6 to 20 carbon atoms, which optionally has one or more substituents, an aralkyl group optionally having oneor more substituents, wherein the aryl moiety in said aralkyl group is an aryl group having 6 to 12 carbon atoms and the alkyl moiety in said aralkyl group is a linear or branched chain alkyl group having 1 to 6 carbon atoms, or a group represented by the formula (a), the formula (b), or the formula (c):

(a)

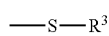
(b)

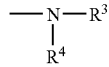
(c)

wherein $R^3$ is a linear or branched chain alkyl group having 1 to 20 carbon atoms, which optionally has one or more substituents, an aryl group having 6 to 20 carbon atoms, which optionally has one or more substituents, or an aralkyl group optionally having one or more substituents, wherein the aryl moiety in said aralkyl group is an aryl group having 6 to 12 carbon atoms and the alkyl moiety in said aralkyl group is a linear or branched chain alkyl group having 1 to 6 carbon atoms, and $R^4$ is a hydrogen atom, a linear or branched chain alkyl group having 1 to 20 carbon atoms, which optionally has one or more substituents, an aryl group having 6 to 20 carbon atoms, which optionally has one or more substituents, or an aralkyl group optionally having one or more substituents, wherein the aryl moiety in said aralkyl group is an aryl group having 6 to 12 carbon atoms and the alkyl moiety in said aralkyl group is a linear or branched chain alkyl group having 1 to 6 carbon atoms.

(5) The method of the above-mentioned (4), wherein $R^2$ is a methyl group, an ethyl group, a phenyl group, a chlorophenyl group, a tolyl group, a benzyl group, a methoxy group, a methylthio group, or a dimethylamino group.

(6) The method of the above-mentioned (1), wherein M is at least one alkali metal atom selected from the group consisting of a potassium atom, a sodium atom, a lithium atom, and mixtures thereof.

(7) The method of the above-mentioned (1), wherein the aminopyrimidine compound is at least one member selected from the group consisting 2-methoxy-6-oxo-5-phenylacetylamino-1,6-dihydropyrimidine; 2-methoxy-6-oxo-5-acetylamino-1,6-dihydropyrimidine; 2-methylthio-6-oxo-5-phenylacetylamino-1,6-dihydropyrimidine; 2-methylthio-6-oxo-5-acetylamino-1,6-dihydropyrimidine; 2-dimethylamino-6-oxo-5-phenylacetylamino-1,6-dihydro pyrimidine; 2-phenyl-6-oxo-5-phenylacetylamino-1,6-dihydropyrimidine; and mixtures thereof.

(8) An aminopyrimidine compound represented by formula (4):

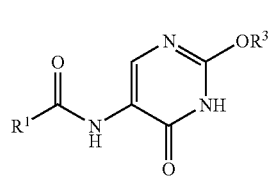
(4)

wherein $R^1$ is an alkyl group optionally having one or more substituents or an aralkyl group optionally having one or more substituents; and $R^3$ is an alkyl group optionally having one or more substituents, an aryl group optionally having one or more substituents or an aralkyl group optionally having one or more substituents, or a salt thereof.

(9) The aminopyrimidine compound of the above-mentioned (8), wherein $R^1$ is a linear or branched chain alkyl group having 1 to 20 carbon atoms, which optionally has one or more substituents, or an aralkyl group optionally having one or more substituents, wherein the aryl moiety in said aralkyl group is an aryl group having 6 to 12 carbon atoms and the alkyl moiety in said aralkyl group is a linear or branched chain alkyl group having 1 to 6 carbon atoms, or a salt thereof.

(10) The aminopyrimidine compound of the above-mentioned (9), wherein $R^1$ is a methyl group, an ethyl group, or a benzyl group, or a salt thereof.

(11) The aminopyrimidine compound of the above-mentioned (8), wherein $R^3$ is a linear or branched chain alkyl group having 1 to 20 carbon atoms, which optionally has one or more substituents, an aryl group having 6 to 20 carbon atoms, which optionally has one or more substituents, or an aralkyl group optionally having one or more substituents, wherein the aryl moiety in said aralkyl group is an aryl group having 6 to 12 carbon atoms and the alkyl moiety in said aralkyl group is a linear or branched chain alkyl group having 1 to 6 carbon atoms, or a salt thereof.

(12) The aminopyrimidine compound of the above-mentioned (11), wherein $R^3$ is a methyl group, an ethyl group, a phenyl group, a chlorophenyl group, a tolyl group, or a benzyl group, or a salt thereof.

(13) The aminopyrimidine compound of the above-mentioned (8), which is selected from the group consisting of 2-methoxy-6-oxo-5-phenylacetylamino-1,6-dihydropyrimidine and 2-methoxy-6-oxo-5-acetylamino-1,6-dihydropyrimidine, or a salt thereof.

The aminopyrimidine compound represented by formula (3) in the present invention can be, when an aminopyrimidine compound represented by following formulae (3a) or (3b), for example, selectively aminated at the 2-position (see, *J. Heterocyclic Chem.*, vol. 19 (5), pp. 1117-1124 (1982) and *J. Chem. Soc., Perk. Trans.* 1, (7), pp. 1659-1664 (1992), and can also be selectively chlorinated at the 4-position (see, *Research Disclosure,* 452068, 10 Dec. 2001 and Ger. Offen., 3423622, 1986). Therefore, various substituents can be introduced into the 2-position and the 4-position of the aminopyrimidine compound to give various compounds:

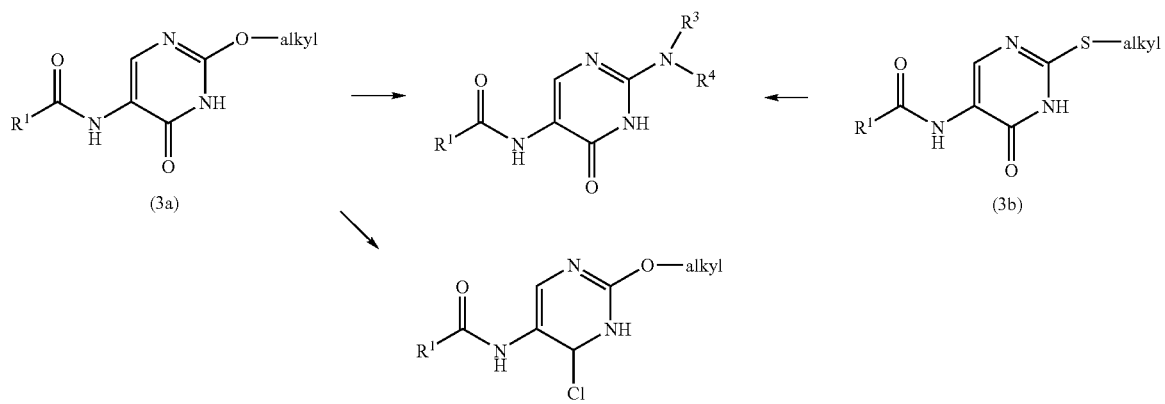

(3a) (3b)

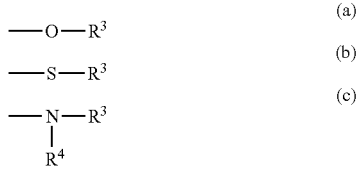

wherein $R^1$, $R^3$ and $R^4$ are as defined above and alkyl is an alkyl group.

Thus, according to the present invention, an aminopyrimidine compound represented by the above-mentioned formula (3), which is useful as an intermediate for producing various compounds having a pharmacological activity, can be efficiently produced.

DETAILED DESCRIPTION OF THE PREFERRED EMBODIMENTS

The definitions of the symbols used in the present invention are as follows.

In the formulae of the present invention, $R^1$ is an alkyl group optionally having one or more substituents or an aralkyl group optionally having one or more substituents. In the formulae of the present invention; moreover, $R^2$ is an alkyl group optionally having one or more substituents, an aryl group optionally having one or more substituents, or a group represented by the formula (a), the formula (b), or the formula (c):

$$—O—R^3 \quad (a)$$
$$—S—R^3 \quad (b)$$
$$—\underset{R^4}{\overset{|}{N}}—R^3 \quad (c)$$

In the formula (a), the formula (b) and the formula (c), $R^3$ is an alkyl group optionally having one or more substituents, an aryl group optionally having one or more substituents or an aralkyl group optionally having one or more substituents; and $R^4$ is a hydrogen atom, an alkyl group optionally having one or more substituents, an aryl group optionally having one or more substituents or an aralkyl group optionally having one or more substituents. Particularly, a group represented by the formula (a) or (b) is preferable.

As the "alkyl group" for $R^1$, $R^2$, $R^3$ or $R^4$, a linear or branched chain alkyl group preferably having 1 to 20, more preferably 1 to 7, carbon atoms can be mentioned. Specifically, for example, alkyl groups such as a methyl group, an ethyl group, an n-propyl group, an isopropyl group, an n-butyl group, an isobutyl group, a sec-butyl group, a tert-butyl group, a lauryl group, and the like can be mentioned. Of these, a methyl group and an ethyl group are preferable.

The alkyl group is optionally substituted by one or more substituents below. As the substituent here, for example, a linear or branched chain alkoxy group (carbon number: 1 to 6, e.g., methoxy group), a halogen atom (e.g., chlorine atom, fluorine atom, and the like), a hydroxyl group, and the like can be mentioned.

The "aralkyl group" for $R^1$, $R^2$, $R^3$ or $R^4$ is an aralkyl group wherein the aryl moiety is preferably an aryl group having 6 to 12, more preferably 6 to 8, carbon atoms and the alkyl moiety is preferably a linear or branched chain alkyl group having 1 to 6, more preferably 1 to 3, carbon atoms. As a specific example of the aralkyl group, a benzyl group is preferable.

The aralkyl group is optionally substituted by one or more substituents below. As the substituents here, for example, a nitro group, a linear or branched chain alkoxy group (carbon number: 1 to 6, e.g.: methoxy group), a halogen atom (e.g., chlorine atom, fluorine atom, and the like), a hydroxyl group, and the like can be mentioned.

As the "aryl group" for $R^1$, $R^2$, $R^3$ or $R^4$, an aryl group preferably having 6 to 20, more preferably 6 to 8, carbon atoms can be mentioned. The aryl group is optionally substituted by one or more substituents below. As the substituents here, for example, a nitro group, a linear or branched chain alkoxy group (carbon number: 1 to 6, e.g., methoxy group), a halogen atom (e.g., chlorine atom, fluorine atom, and the like), a linear or branched chain alkyl group (preferable carbon number: 1 to 4, e.g., methyl group, ethyl group, propyl group, and the like), a hydroxyl group, and the like can be mentioned. Specific examples of the aryl group optionally having one or more substituents include a phenyl group, an o-, m- or p-nitrophenyl group, an o-, m- or p-methoxyphenyl group, an o-, m- or p-chlorophenyl group, an o-, m- or p-fluorophenyl group, an o-, m- or p-tolyl group, and the like can be mentioned. As $R^1$, a phenyl group, a p-methoxyphenyl group, a p-chlorophenyl group and a tolyl group are particularly preferable and as $R^2$, $R^3$ and $R^4$, a phenyl group, a chlorophenyl group and a tolyl group are particularly preferable.

In the formulae of the present invention, M is a hydrogen atom or an alkali metal atom, and as the alkali metal atom, a potassium atom, a sodium atom, and a lithium atom can be mentioned. Particularly, a sodium atom and a potassium atom are preferable.

The azlactone compound represented by formula (1), which is used as a starting material in the present invention, can be obtained by, for example, hydrolysis of a compound represented by the following formula (5) in water or a mixed solvent of water and an organic solvent, in the presence of an alkali metal hydroxide. To be specific, for example, an alkali metal hydroxide, preferably an aqueous solution thereof, is added to compound (5) in a solvent, wherein the order of addition may be reverse or simultaneous:

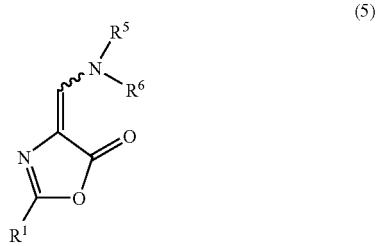

(5)

wherein $R^1$ is as defined above, $R^5$ and $R^6$ are the same or different and each is a methyl group or an ethyl group, and a wavy line indicates a cis form a trans form, or a mixture thereof.

As the alkali metal hydroxide to be used, sodium hydroxide, potassium hydroxide, lithium hydroxide, and the like can be mentioned, with preference given to sodium hydroxide. The alkali metal hydroxide may be used in the form of a solid but preferably used as an aqueous solution, wherein the concentration thereof is within the range of 0.1N to 8N.

The amount of the alkali metal hydroxide to be used is generally 0.9-1.8 molar equivalents, preferably 1-1.3 molar equivalents, relative to the moles of compound (5).

The solvent may be any as long as it does not inhibit the reaction and, for example, water, acetates (e.g., ethyl acetate, isopropyl acetate, isobutyl acetate, n-butyl acetate, and the like), acetonitrile, tetrahydrofuran (THF), N,N-dimethylformamide, acetone, and the like can be mentioned. These may be used alone or in a combination of two or more kinds thereof, wherein a mixed solvent of water and an organic solvent miscible with water, such as acetonitrile, acetone and the like is more preferable, and a mixed solvent of acetonitrile and water is particularly preferable. The amount of the solvent to be used is generally 3- to 50-fold by weight, preferably 5- to 20-fold by weight, relative to the weight of compound (5). When an aqueous alkali metal hydroxide solution is used, the amount of water is included in the amount of the solvent. When an alcohol solvent (e.g., methanol, ethanol, isopropyl alcohol, and the like) is used, a side reaction such as azlactone ring opening of compound (5) and the like tends to occur, and use of an alcohol solvent is not preferable.

The reaction temperature is within the range of from generally 0° C. to the refluxing temperature of the solvent (preferably 0 to 30° C.) to be used. This reaction is completed within the above-mentioned temperature range in generally 60 min to overnight (preferably 2 hours to 20 hours).

After the completion of the reaction, compound (1) is present in the form of an alkali metal salt (M=alkali metal). When a free form of compound (1) (M=hydrogen atom) is to be isolated, an acid (e.g., hydrochloric acid, sulfuric acid, etc.) is added to the reaction mixture to adjust its pH to 3 to 5, and the mixture is subjected to conventional isolation and purification methods, such as concentration of the reaction mixture or addition of a crystallization solvent to allow crystal precipitation or silica gel column chromatography to isolate a free form of compound (1). As a crystallization solvent for the crystal precipitation, water, ethers (e.g., diethyl ether, THF, and the like), acetone, acetonitrile, hydrocarbon solvents (e.g., toluene, benzene, hexane, heptane, and the like), halogen solvents (e.g., dichloromethane, dichloroethane, and the like), water or a mixed solvent thereof, and the like can be mentioned. For isolation in the form of an alkali metal salt, conventional isolation and purification methods, such as concentration of a reaction mixture or addition of the above-mentioned crystallization solvent to allow crystal precipitation, are applied to isolate an alkali metal salt of compound (1).

Since an alkali metal salt of compound (1) easily forms a hydrate, it is preferably dried at a high temperature or dried by washing with a high temperature slurry in an organic solvent to give an anhydrous crystal.

Compound (5) can be produced by a known method. For example, as in Reference Examples 1-3 to be mentioned later, N-acylglycine represented by the formula: $R^1C(=O)NHCH_2COOH$, wherein $R^1$ is as defined above, is reacted with formamide represented by the formula: $R^5R^6NCHO$ (wherein each symbol is as defined above) and phosphorus oxychloride to give compound (5) (Ind. J. Chem., vol. 39B, pp. 688-693 (2000)). In addition, as shown in Reference Example 4 to be mentioned later, N-acylglycine represented by the formula: $R^1C(=O)NHCH_2COOH$ (wherein $R^1$ is as defined above) is reacted with formamidedimethylacetal represented by the formula: $R^5R^6NCH(OMe)_2$ (wherein each symbol is as defined above) in the presence of N,N'-dicyclohexylcarbodiimide to give compound (4) (J. Heterocyclic Chem., vol. 34, pp. 247 (1997)).

In the present invention, an azlactone compound represented by formula (1) is reacted with an amidine compound represented by formula (2) or a salt thereof to give an aminopyrimidine compound represented by formula (3).

The solvent to be used for the reaction may be any as long as it does not inhibit the reaction and, for example, acetates (e.g., ethyl acetate, isopropyl acetate, isobutyl acetate, n-butyl acetate, and the like), alcohol, acetonitrile, acetone, tetrahydrofuran (THF), N,N-dimethylformamide, and the like can be mentioned. One or more kinds of these may be used in combination. Particularly, water-soluble organic solvents such as acetonitrile, acetone, and the like are preferable. Of these, acetonitrile is more preferable. The amount of the solvent to be used is generally 3- to 50-fold by weight, preferably 5- to 20-fold by weight, relative to the weight of the azlactone compound (1). The amount of the amidine compound (2) or a salt thereof to be used is generally 0.8 to 3.0 molar equivalents, more preferably 1.0 to 1.5 molar equivalents, relative to the moles of azlactone compound (1).

The reaction temperature is generally 0° C. to 100° C., preferably 30° C. to 80° C. This reaction is completed within the above-mentioned temperature range in generally 1 to 30 hours, preferably 3 to 24 hours.

The type of salt of the amidine compound represented by formula (2) is not particularly limited, but hydrochloride, sulfate, bromate, and the like can be preferably mentioned. An amidine compound represented by formula (2) is preferably used in the form of a stable salt.

A method of isolating the obtained compound (3) after the completion of the reaction is not particularly limited, and various methods known to those of ordinary skill in the art can be used. Generally, since a compound (3) is crystallized during-the reaction, for example, a compound (3) can be isolated by, after the completion of the reaction, collecting the crystals by filtration and washing the crystals with water, or, where necessary, collecting the crystals by filtration after adding water to the reaction solution to partition a salt into a mother liquor, or, where necessary, washing the filtered crystals with water and drying the separated crystals. In addition, before collection of the crystals by filtration, the reaction solution may be concentrated, cooled, a poor solvent may be added and the like to perform further crystallization.

Among the compounds of formula (3), the compounds represented by formula (4) are novel substances:

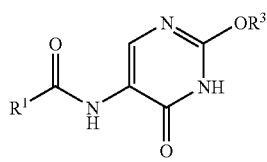

(4)

wherein $R^1$ and $R^3$ are as defined above.

As noted above, the compounds of formula (3) are useful as intermediates for preparing antineoplastic agents. In particular, the present invention provides methods for preparing compounds of formula (6):

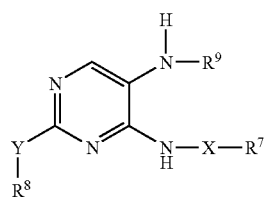

(6)

wherein:

X is selected from the group consisting of a direct bond, $C_{1-4}$ alkylene, $C_{1-4}$ alkyleneoxy, $C_{1-4}$ alkoxyphenyl, or phenyl $C_{1-4}$ alkylene;

Y is selected from the group consisting of a direct bond or $C_{1-2}$ alkyl;

$R^7$ is selected from the group consisting of (i) 5-15 membered cyclic or branched chain heterocompound which includes one or two selected from a group consisting of nitrogen, oxygen and sulfur and which is substituted with one or two selected from a group consisting of hydrogen, halogen, nitro, hydroxy, $C_{1-6}$ alkyl, $C_{3-6}$ alkenyl and halogen $C_{1-4}$ alkoxy, (ii) $C_{4-10}$ carbocyclic compound or (iii) hydroxy $C_{1-4}$ alkoxy;

$R^8$ is selected from the group consisting of 5-15 membered cyclic or branched chain heterocompound which includes one or two selected from a group consisting of nitrogen, oxygen and sulfur and which is substituted with one or two selected from a group consisting of hydrogen, hydroxy, halogen, nitro, hydroxy $C_{1-5}$ alkyl $C_{1-6}$ alkyl, $C_{3-6}$ alkenyl, and halogen $C_{1-4}$;

$R^9$ is selected from the group consisting of hydrogen, —C(O) $R^{10}$, or —S(O)$_2R^{11}$;

$R^{10}$ and $R^{11}$ are each independently selected from the group consisting of hydroxy, $C_{1-6}$ alkyl, $C_{3-7}$ cycloalkyl, $C_{3-6}$ alkenyl, halogen $C_{1-6}$ alkyl, halogen, $C_{2-6}$ alkenyl and $C_{1-4}$ alkoxy; or $R^{10}$ and $R^{11}$ represent each independently:

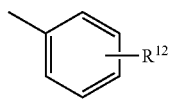

and $R^{12}$ is selected from a group consisting of hydrogen, hydroxy, $C_{1-6}$ alkyl, $C_{3-6}$ alkenyl, halogen, $C_{1-6}$ alkyl, halogen, nitro and $C_{1-4}$ alkoxy. Such compounds and preferred embodiments are described in U.S. Pat. No. 6,380,206 which is incorporated herein by reference.

Other features of the invention will become apparent in the course of the following descriptions of exemplary embodiments which are given for illustration of the invention and are not intended to be limiting thereof.

EXAMPLES

Reference Example 1

4-(N,N-dimethylaminomethylene)-2-methyl-5-oxazolinone

Phosphorus oxychloride (67.0 g, 437 mmol) and N,N-dimethylformamide (33.0 g, 451 mmol) were added to N-acetylglycine (20.0 g, 171 mmol) in an ice bath, and the mixture was stirred at 45° C. for 1.5 hours. The reaction mixture was concentrated under reduced pressure and added dropwise to 28% aqueous ammonia (150 ml) while maintaining the temperature at not higher than 10° C. The reaction mixture was stirred for 1 hour in an ice-bath and the precipitate was collected by filtration. The obtained crystals were washed successively with water and ethanol and dried to give the title compound as crystals (20.2 g, 131 mmol).

$^1$H-NMR (CDCl$_3$) δ: 2.21(3H, s), 3.18(3H, m), 3.47(3H, s), 6.96(1H, s)

MS (ESI) m/z [MH]$^+$155.2

Reference Example 2

2-benzyl-4-(N,N-dimethylaminomethylene)-5-oxazolinone

Chloroform (30.0 ml), phosphorus oxychloride (20.0 g, 130 mmol), and N,N-dimethylformamide (10.0 g, 137 mmol) were added to phenaceturic acid (10.0 g, 51.8 mmol) in an ice-bath, and the mixture was stirred at 45° C. for 1.5 hours. The reaction mixture was concentrated under reduced pressure and added dropwise to 28% aqueous ammonia (65 ml) while maintaining the temperature at not higher than 10° C. The mixture was extracted with chloroform, and the organic layer was washed with water and saturated brine and then concentrated to dryness. The concentrate was washed with isopropyl alcohol. The crystals were collected by filtration, washed with isopropyl alcohol, and dried to give the title compound as crystals (9.90 g, 43.3 mmol).

$^1$H-NMR(CDCl$_3$) δ: 3.17(3H, s), 3.48(3H, m), 3.83(2H, s), 6.97(1H, s), 7.23-7.36(5H, m)

MS (ESI) m/z [MH]$^+$231.5

Reference Example 3

2-benzyl-4-(N,N-dimethylaminomethylene)-5-oxazolinone

Toluene (10.0 ml) and N,N'-dicyclohexylcarbodiimide (1.07 g, 5.19 mmol) were added to phenaceturic acid (1.00 g, 5.18 mmol), and the mixture was stirred overnight at room temperature. The precipitate was removed by filtration, N,N-dimethylformamide-dimethylacetal (0.68 g, 5.71 mmol) was added, and the mixture was stirred overnight. The reaction mixture was washed with saturated brine and concentrated to dryness. Isopropyl alcohol was added to the concentrate to allow crystallization and the precipitated crystals were collected by filtration. The crystals were washed with isopropyl alcohol and vacuum dried to give the title compound as crystals (0.78 g, 3.39 mmol).

Reference Example 4

4-hydroxymethylene-2-methyl-5-oxazolinone sodium salt-anhydride

2N Aqueous sodium hydroxide solution (15 ml, 30.0 mmol) was added to a solution (50 ml) of 4-(N,N-dimethylaminomethylene)-2-methyl-5-oxazolinone (4.00 g, 26.0 mmol) in acetonitrile with ice-cooling, and the mixture was stirred overnight. Water was evaporated, acetonitrile (30 ml) was added, and the mixture was stirred at 60° C. for 1 hour. The precipitate was collected by filtration, washed with acetonitrile, and vacuum dried at 80° C. to give the tide compound as white crystals (3.65 g, 24.5 mmol).
$^1$H-NMR (DMSO-$d_6$) δ: 2.00(3H, s), 8.67(3H, s)
MS (API-ES) m/z [MH]$^+$126.1

Reference Example 5

2-benzyl-4-hydroxymethylene-5-oxazolinone sodium salt-monohydrate

1N Aqueous sodium hydroxide solution (53 ml, 53.0 mmol) was added to a solution (120 ml) of 2-benzyl-4-(N,N-dimethylaminomethylene)-5-oxazolinone (10.8 g, 46.9 mmol) in acetonitrile with ice-cooling, and the mixture was stirred overnight. Acetonitrile was evaporated to allow precipitation of crystals with ice-cooling. The precipitate was collected by filtration and vacuum dried to give the title compound as white crystals (5.99 g, 26.6 mmol). Differential Scanning Calorymetry (DSC) and Thermogravimetry (TG) were performed using a thermal analysis instrument (RIGAKU CORPORATION, TAS-200). As a result, an endothermal peak was found at 121.4° C. and a weight decrease was observed at 116.1 to 126.9° C.
$^1$H-NMR (DMSO-$d_6$) δ: 3.66(2H, s), 7.22-7.32(5H, m), 8.71(1H, s)
MS (ESI) m/z [MH]$^-$202.1

Reference Example 6

2-benzyl-4-hydroxymethylene-5-oxazolinone sodium salt-anhydride

1N Aqueous sodium hydroxide solution (5 ml, 5.00 mmol) was added to a solution (10 ml) of 2-benzyl-4-(N,N-dimethylaminomethylene)-5-oxazolinone (1.00 g, 4.34 mmol) in acetonitrile with ice-cooling, and the mixture was stirred overnight. The reaction mixture was concentrated to dryness, and acetonitrile (5 ml) was added. The precipitate was collected by filtration and dried at 100° C. for 2 hours to give the title compound as white crystals (0.90 g, 4.00 mmol). DSC and TG were performed using a thermal analysis instrument. As a result, endothermal peak and clear weight change were not observed up to 220° C.
$^1$H-NMR (DMSO-$d_6$) δ: 3.66(2H, s), 7.22-7.32(5H, m), 8.71(1H, s)
MS (ESI) m/z [MH]$^-$202.1

Reference Example 7

2-benzyl-4-hydroxymethylene-5-oxazolinone

2N Aqueous sodium hydroxide solution (0.92 ml) was added to a solution (15 ml) of 4-N,N'-dimethylaminomethylene-2-benzyl-5-oxazoline (350 mg, 6.65 mmol) in acetonitrile with ice-cooling, and the mixture was stirred overnight at room temperature. The reaction mixture was concentrated to allow evaporation of acetonitrile, washed with ethyl acetate (5 ml), and adjusted to pH 4 with 1N hydrochloric acid with ice-cooling. The precipitate was collected by filtration, washed with water, and vacuum dried to give the title compound as crystals (1.03 g, 5.07 mmol).
$^1$H-NMR (DMSO-$d_6$) δ: 3.92(2H, s), 7.29-7.38(5H, m), 7.68 (1H, s)
MS (ESI) m/z [MH]$^-$202.3

Example 1

Acetonitrile (15 ml) was added to 2-benzyl-4-hydroxymethylene-5-oxazolone sodium salt (1.00 g, 4.44 mmol) and O-methylisourea hydrochloride (0.49 g, 4.44 mmol), and the mixture was stirred overnight at 80° C. The mixture was concentrated under reduced pressure, water (5 ml) was added, and the mixture was stirred at room temperature for 1 hour. Then, the precipitate was collected by filtration and vacuum dried to give 2-methoxy-6-oxo-5-phenylacetylamino-1,6-dihydropyrimidine (0.94 g, 3.64 mmol).
$^1$H-NMR (DMSO-$d_6$) δ: 3.75(2H, s), 3.85(3H), 7.23-7.31 (5H, m), 8.40(1H, s), 9.32(1H, s), 12.66(1H, brs)
MS (ESI) m/z [MH]$^+$259.9

Example 2

Acetonitrile (20 ml) was added to 2-methyl-4-hydroxymethylene-5-oxazolone sodium salt (1.00 g, 6.71 mmol) and O-methylisourea hydrochloride (0.74 g, 6.71 mmol), and the mixture was stirred at 80° C. for 2 days. The mixture was concentrated, and methanol (5 ml) and water (3 ml) were added. The mixture was stirred at room temperature for 1 hour. Then, the precipitate was collected by filtration and vacuum dried to give 2-methoxy-6-oxo-5-acetylamino-1,6-dihydropyrimidine (0.91 g, 4.97 mmol).
$^1$H-NMR (DMSO-$d_6$) δ: 2.06(3H, s), 3.85(3H), 8.36 (1H, s), 9.14(1H, s), 12.62(1H, brs)
MS (ESI) m/z [MH]$^-$182.1

Example 3

O-Methylisourea hydrochloride (0.11 g, 1.0 mmol) was dissolved in methanol (2 ml), and 28% sodium methoxide (0.19 g, 1.0 mmol) was added. Acetonitrile was added, and the mixture was concentrated. 2-Benzyl-4-hydroxymethylene-5-oxazolone (0.203 g, 1.00 mmol) was added, and the mixture was stirred overnight at 80° C. Water (3 ml) was added, and the mixture was stirred at room temperature for 1 hour. Then, the precipitate was collected by filtration and vacuum dried to give 2-methoxy-6-oxo-5-phenylacetylamino-1,6-dihydropyrimidine (0.16 g, 0.62 mmol). The values of the shift in $^1$H-NMR were the same as those in Example 1.

Example 4

Acetonitrile (6 ml) was added to 2-benzyl-4-hydroxymethylene-5-oxazolone sodium salt (0.50 g, 2.22 mmol) and S-methylisourea sulfate (0.34 g, 1.22 mmol), and the mixture was stirred overnight at 80° C. The mixture was cooled and the precipitate was collected by filtration. The crystals were washed with water, and the obtained crystals were vacuum dried to give 2-methylthio-6-oxo-5-phenylacetylamino-1,6-dihydropyrimidine (0.51 g, 1.91 mmol).

$^1$H-NMR (DMSO-$d_6$) δ: 2.74(3H, s), 3.77(2H, s), 7.23-7.32(5H, m), 8.60(1H, s), 9.43(1H, s), 13.03(1H, brs)
MS (ESI) m/z [MH]$^-$274.0

Example 5

Acetonitrile (6 ml) was added to 2-methyl-4-hydroxymethylene-5-oxazolone sodium salt (0.10 g, 0.67 mmol) and S-methylisourea sulfate (0.10 g, 0.37 mmol), and the mixture was stirred overnight at 80° C. The mixture was cooled, and the precipitate was collected by filtration. The crystals were washed with water and the obtained crystals were vacuum dried to give 2-methylthio-6-oxo-5-acetylamino-1,6-dihydropyrimidine (0.09 g, 0.46 mmol).
$^1$H-NMR (DMSO-$d_6$) δ: 2.08(3H, s), 2.48(3H, s), 8.58 (1H, s), 9.27(1H, s), 12.96 (1H, brs)
MS (ESI) m/z [MH]$^-$197.9

Example 6

Acetonitrile (2 ml) was added to 2-benzyl-4-hydroxymethylene-5-oxazolone sodium salt (61 mg, 0.27 mmol) and N-dimethylguanidine sulfate (40 mg, 0.15 mmol), and the mixture was stirred overnight at 85° C. Water (3 ml) was added, and the mixture was stirred at room temperature for 1 hour. Then, the precipitate was collected by filtration and vacuum dried to give 2-dimethylamino-6-oxo-5-phenylacetylamino-1,6-dihydropyrimidine (45 mg, 0.17 mmol).
$^1$H-NMR (DMSO-$d_6$) δ: 2.99(6H, s), 3.71(2H), 7.23-7.31 (5H, m), 8.21(1H, s), 9.09(1H, brs)
MS (ESI) m/z [MH]$^-$271.2

Example 7

Acetonitrile (6 ml) was added to 2-benzyl-4-hydroxymethylene-5-oxazolone sodium salt (0.50 g, 2.22 mmol) and benzamidine hydrochloride (0.35 g, 2.22 mmol), and the mixture was stirred overnight at 80° C. Water (3 ml) was added, and the mixture was stirred. The precipitate was collected by filtration, and the obtained crystals were washed with water and vacuum dried to give 2-phenyl-6-oxo-5-phenylacetylamino-1,6-dihydropyrimidine (0.51 g, 1.67 mmol).
$^1$H-NMR (DMSO-$d_6$) δ: 3.84(2H, s), 7.25-7.34(5H, m), 7.51(3H, m), 8.06(2H, d, J=7.0 Hz), 8.86(1H, s), 9.64(1H, s), 13.05(1H, brs)
MS (ESI) m/z [MH]$^+$306.5

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A method for producing a compound represented by formula (3):

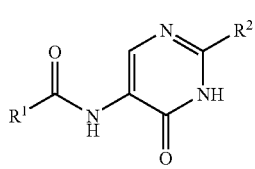

wherein $R^1$ is an alkyl group optionally having one or more substituents, an aryl group optionally having one or more substituents or an aralkyl group optionally having one or more substituents; and $R^2$ is an alkyl group optionally having one or more substituents, an aryl group optionally having one or more substituents, an aralkyl group optionally having one or more substituents, or a group represented by the formula (a), the formula (b), or the formula (c):

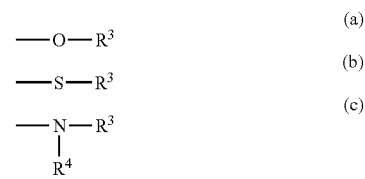

wherein $R^3$ is an alkyl group optionally having one or more substituents, an aryl group optionally having one or more substituents, or an aralkyl group optionally having one or more substituents; and $R^4$ is a hydrogen atom, an alkyl group optionally having one or more substituents, an aryl group optionally having one or more substituents or an aralkyl group optionally having one or more substituents,
wherein said method comprises reacting a compound represented by formula (1):

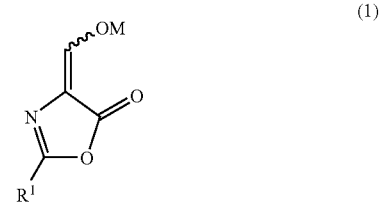

wherein M is a hydrogen atom or an alkali metal atom; a wavy line represents a cis form, a trans form, or a mixture thereof; and $R^1$ is as defined above, with a compound represented by formula (2):

wherein $R^2$ is as defined above, or a salt thereof.

2. The method of claim 1, wherein $R^1$ is a linear or branched chain alkyl group having 1 to 20 carbon atoms, which optionally has one or more substituents, an aryl group having 6 to 20 carbon atoms or an aralkyl group optionally having one or more substituents, wherein the aryl moiety in said aralkyl group is an aryl group having 6 to 12 carbon atoms and the alkyl moiety in said aralkyl group is a linear or branched chain alkyl group having 1 to 6 carbon atoms.

3. The method of claim 2, wherein $R^1$ is a methyl group, an ethyl group, or a benzyl group.

4. The method of claim 1, wherein $R^2$ is a linear or branched chain alkyl group having 1 to 20 carbon atoms, which optionally has one or more substituents, an aryl group having 6 to 20 carbon atoms, which optionally has one or more substituents, an aralkyl group optionally having one or more substituents, wherein the aryl moiety in said aralkyl group is an aryl group having 6 to 12 carbon atoms and the alkyl moiety in said aralkyl group is a linear or branched chain alkyl group having 1 to 6 carbon atoms, or a group represented by the formula (a), the formula (b) or the formula (c):

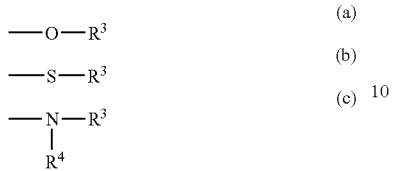

wherein $R^3$ is a linear or branched chain alkyl group having 1 to 20 carbon atoms, which optionally has one or more substituents, an aryl group having 6 to 20 carbon atoms, which optionally has one or more substituents, or an aralkyl group optionally having one or more substituents, wherein the aryl moiety in said aralkyl group is an aryl group having 6 to 12 carbon atoms and the alkyl moiety in said aralkyl group is a linear or branched chain alkyl group having 1 to 6 carbon atoms; and $R^4$ is a hydrogen atom, a linear or branched chain alkyl group having 1 to 20 carbon atoms, which optionally has one or more substituents, an aryl group having 6 to 20 carbon atoms, which optionally has one or more substituents, or an aralkyl group optionally having one or more substituents, wherein the aryl moiety in said aralkyl group is an aryl group having 6 to 12 carbon atoms and the alkyl moiety in said aralkyl group is a linear or branched chain alkyl group having 1 to 6 carbon atoms.

5. The method of claim 4, wherein $R^2$ is a methyl group, an ethyl group, a phenyl group, a chlorophenyl group, a tolyl group, a benzyl group, a methoxy group, a methylthio group, or a dimethylamino group.

6. The method of claim 1, wherein M is at least one alkali metal atom selected from the group consisting of a potassium atom, a sodium atom, a lithium atom, and mixtures thereof.

7. The method of claim 1, wherein the aminopyrimidine compound is selected from the group consisting of 2-methoxy-6-oxo-5-phenylacetylamino-1,6-dihydropyrimidine; 2-methoxy-6-oxo-5-acetylamino-1,6-dihydropyrimidine; 2-methylthio-6-oxo-5-phenylacetylamino-1,6-dihydropyrimidine; 2-methylthio-6-oxo-5-acetylamino-1,6-dihydroyrimidine; 2-dimethylamino-6-oxo-5-phenylacetylamino-1,6-dihydropyrimidine; and 2-phenyl-6-oxo-5-phenylacetylamino-1,6-dihydropyrimidine.

8. In a method of producing a compound of formula (6):

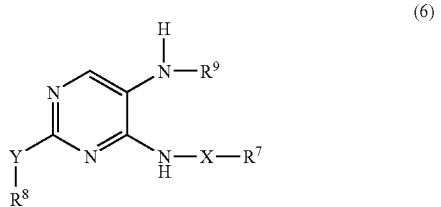

wherein:
X is selected from the group consisting of a direct bond, $C_{1-4}$ alkylene, $C_{1-4}$ alkyleneoxy, $C_{1-4}$ alkoxyphenyl, or phenyl $C_{1-4}$ alkylene;
Y is selected from the group consisting of a direct bond or $C_{1-2}$ alkyl;

$R^7$ is selected from the group consisting of (i) 5-15 membered cyclic or branched chain heterocompound which includes one or two selected from a group consisting of nitrogen, oxygen and sulfur and which is substituted with one or two selected from a group consisting of hydrogen, halogen, nitro, hydroxy, $C_{1-6}$ alkyl, $C_{3-6}$ alkenyl and halogen $C_{1-4}$ alkoxy, (ii) $C_{4-10}$ carbocyclic compound or (iii) hydroxy $C_{1-4}$ alkoxy;

$R^8$ is selected from the group consisting of 5-15 membered cyclic or branched chain heterocompound which includes one or two selected from a group consisting of nitrogen, oxygen and sulfur and which is substituted with one or two selected from a group consisting of hydrogen, hydroxy, halogen, nitro, hydroxy $C_{1-5}$ alkyl $C_{1-6}$ alkyl, $C_{3-6}$ alkenyl, and halogen $C_{1-4}$;

$R^9$ is selected from the group consisting of hydrogen, —C(O)$R^{10}$, or —S(O)$_2 R^{11}$;

$R^{10}$ and $R^{11}$ are each independently selected from the group consisting of hydroxy, $C_{1-6}$ alkyl, $C_{3-7}$ cycloalkyl, $C_{3-6}$ alkenyl, halogen $C_{1-6}$ alky, halogen, $C_{2-6}$ alkenyl and $C_{1-4}$ alkoxy; or $R^{10}$ and $R^{11}$ represent each independently:

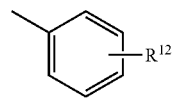

and $R^{12}$ is selected from a group consisting of hydrogen, hydroxy, $C_{1-6}$ alkyl, $C_{3-6}$ alkenyl, halogen, $C_{1-6}$ alkyl, halogen, nitro and $C_{1-4}$ alkoxy, which method comprises converting a compound of formula (3):

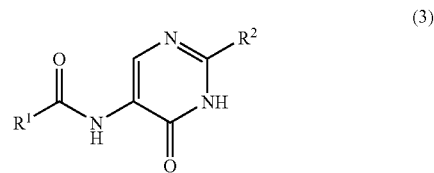

wherein $R^1$ is an alkyl group optionally having one or more substituents, an aryl group optionally having one or more substituents or an aralkyl group optionally having one or more substituents; and $R^2$ is an alkyl group optionally having one or more substituents, an aryl group optionally having one or more substituents, an aralkyl group optionally having one or more substituents, or a group represented by the formula (a), the formula (b), or the formula (c):

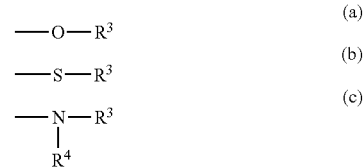

wherein $R^3$ is an alkyl group optionally having one or more substituents, an aryl group optionally having one or more substituents, or an aralkyl group optionally having one or more substituents; and $R^4$ is a hydrogen atom, an alkyl group optionally having one or more substituents, an aryl group optionally having one or more substituents or an aralkyl group optionally having one or more substituents, to said compound of formula (6), the improvement being said compound of formula (3) is prepared by a method according to claim 1.

9. The method of claim 8, wherein $R^1$ is a linear or branched chain alkyl group having 1 to 20 carbon atoms, which optionally has one or more substituents, an aryl group having 6 to 20 carbon atoms, which optionally has one or more substituents or an aralkyl group optionally having one or more substituents, wherein the aryl moiety in said aralkyl group is an aryl group having 6 to 12 carbon atoms and the alkyl moiety in said aralkyl group is a linear or branched chain alkyl group having 1 to 6 carbon atoms.

10. The method of claim 9, wherein $R^1$ is a methyl group, an ethyl group, or a benzyl group.

11. The method of claim 8, wherein $R^2$ is a linear or branched chain alkyl group having 1 to 20 carbon atoms, which optionally has one or more substituents, an aryl group having 6 to 20 carbon atoms, which optionally has one or more substituents, an aralkyl group optionally having one or more substituents, wherein the aryl moiety in said aralkyl group is an aryl group having 6 to 12 carbon atoms and the alkyl moiety in said aralkyl group is a linear or branched chain alkyl group having 1 to 6 carbon atoms, or a group represented by the formula (a), the formula (b) or the formula (c):

(a)

-continued

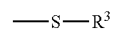
(b)

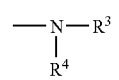
(c)

wherein $R^3$ is a linear or branched chain alkyl group having 1 to 20 carbon atoms, which optionally has one or more substituents, an aryl group having 6 to 20 carbon atoms, which optionally has one or more substituents, or an aralkyl group optionally having one or more substituents, wherein the aryl moiety in said aralkyl group is an aryl group having 6 to 12 carbon atoms and the alkyl moiety in said aralkyl group is a linear or branched chain alkyl group having 1 to 6 carbon atoms; and $R^4$ is a hydrogen atom, a linear or branched chain alkyl group having 1 to 20 carbon atoms, which optionally has one or more substituents, an aryl group having 6 to 20 carbon atoms, which optionally has one or more substituents, or an aralkyl group optionally having one or more substituents, wherein the aryl moiety in said aralkyl group is an aryl group having 6 to 12 carbon atoms and the alkyl moiety in said aralkyl group is a linear or branched chain alkyl group having 1 to 6 carbon atoms.

12. The method of claim 11, wherein $R^2$ is a methyl group, an ethyl group, a phenyl group, a chlorophenyl group, a tolyl group, a benzyl group, a methoxy group, a methylthio group, or a dimethylamino group.

\* \* \* \* \*